US007062327B2

(12) United States Patent
Bradley et al.

(10) Patent No.: US 7,062,327 B2
(45) Date of Patent: Jun. 13, 2006

(54) METHOD AND APPARATUS FOR PROVIDING ATRIAL AUTOCAPTURE IN A DYNAMIC ATRIAL OVERDRIVE PACING SYSTEM FOR USE IN AN IMPLANTABLE CARDIAC STIMULATION DEVICE

(75) Inventors: Kerry Bradley, Glendale, CA (US); Laurence S. Sloman, West Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 749 days.

(21) Appl. No.: 10/138,438

(22) Filed: May 2, 2002

(65) Prior Publication Data
US 2003/0208241 A1 Nov. 6, 2003

(51) Int. Cl.
*A61N 1/36* (2006.01)
(52) U.S. Cl. ....................................... 607/27
(58) Field of Classification Search ............ 607/27, 607/4, 14, 28, 17
See application file for complete search history.

(56) References Cited

U.S. PATENT DOCUMENTS

| 4,712,555 | A | | 12/1987 | Thornander et al. .. 128/419 PG |
| 4,940,052 | A | | 7/1990 | Mann et al. .......... 128/419 PG |
| 4,944,298 | A | | 7/1990 | Sholder .............. 128/419 PG |
| 5,350,401 | A | * | 9/1994 | Levine ........................ 607/4 |
| 5,466,254 | A | | 11/1995 | Helland ...................... 607/123 |
| 5,766,229 | A | * | 6/1998 | Bornzin ....................... 607/28 |
| 2003/0065365 | A1 | * | 4/2003 | Zhu et al. .................... 607/17 |
| 2003/0125777 | A1 | * | 7/2003 | Ding et al. ................... 607/27 |

* cited by examiner

*Primary Examiner*—George Manuel
*Assistant Examiner*—Dana D. Greene

(57) ABSTRACT

Techniques for providing capture verification during overdrive pacing are described. If an overdrive pacing pulse fails to evoke capture (i.e. a loss of capture occurs), a high voltage backup pulse is automatically delivered. Once a second loss of capture occurs during a single sequence of overdrive pacing pulses, an overdrive pulse capture threshold detection search, described herein, is performed while overdrive pacing continues. Various techniques for providing rate recovery are also described herein. The rate recovery techniques are designed to avoid problems that might arise from possible fusion of intrinsic beats and overdrive pacing pulses that fail to evoke capture. In a first rate recovery technique, capture detection is suspended during rate recovery due to the possibility of fusion. Instead, an extra safety margin is added to the overdrive pulses. Once two intrinsic beats are detected, automatic capture verification is reactivated for the next two beats to verify capture before the new overdrive rate is finally established. In a second rate recovery technique, capture verification is maintained throughout rate recovery but the pulse magnitude is increased to a high output mode voltage to avoid any risks of fusion. After the output is increased to the high output mode voltage, a subsequent loss of capture is considered to be an intrinsic event for the purposes of terminating rate recovery. In a third rate recovery technique, capture verification is maintained during rate recovery and the output energy is not increased to the high output mode voltage unless loss of capture is first detected. Subsequent loss of capture events are then counted as P-waves.

23 Claims, 7 Drawing Sheets

METHOD AND APPARATUS FOR PROVIDING ATRIAL AUTOCAPTURE IN A DYNAMIC ATRIAL OVERDRIVE PACING SYSTEM FOR USE IN AN IMPLANTABLE CARDIAC STIMULATION DEVICE

FIELD OF THE INVENTION

The invention generally relates to implantable cardiac stimulation devices such as pacemakers or implantable cardioverter defibrillators (ICDs), and in particular, to techniques for overdrive pacing heart tissue to prevent or terminate arrhythmias.

BACKGROUND OF THE INVENTION

An arrhythmia is an abnormal heart beat pattern. One example of arrhythmia is bradycardia wherein the heart beats at an abnormally slow rate or wherein significant pauses occur between consecutive beats. Other examples of arrhythmias include tachyarrhythmias wherein the heart beats at an abnormally fast rate. With atrial tachycardia, the atria of the heart beat abnormally fast. With ventricular tachycardia, the ventricles of the heart beat abnormally fast. Though often unpleasant for the patient, a tachycardia is typically not fatal. However, some types of tachycardia, particularly ventricular tachycardia, can trigger ventricular fibrillation wherein the heart beats chaotically such that there is little or no net flow of blood from the heart to the brain and other organs. Ventricular tachycardia, if not terminated, is fatal. Hence, it is highly desirable to prevent or terminate arrhythmias, particularly ventricular tachycardia.

One technique for preventing or terminating arrhythmias is to overdrive pace the heart wherein a implantable cardiac stimulation device, such as a pacemaker or implantable cardioverter defibrillator (ICD), applies electrical pacing pulses to the heart at a rate somewhat faster than the intrinsic heart rate of the patient. For bradycardia, the cardiac stimulation device may be programmed to artificially pace the heart at a rate of 60 to 80 pulses per minute (ppm) to thereby prevent the heart from beating too slow and to eliminate any long pauses between heartbeats. To prevent tachyarrhythmias from occurring, the cardiac stimulation device artificially paces the heart at a rate slightly faster than the intrinsic tachyarrhythmia heart rate of the patient. In other words, a slight artificial tachycardia is induced and maintained in an effort to prevent an actual tachycardia from arising. If an actual tachycardia occurs, such as a supraventricular tachycardia (SVT) wherein the heart may begin beating suddenly at 150 beats per minute (bpm) or more, the cardiac stimulation device senses tachycardia and immediately begins pacing at a rate of slightly faster than the tachycardia, then slowly decreases the pacing rate in an effort to slowly reduce the heart rate back to a normal resting rate thereby terminating the tachycardia.

In one exemplary technique, the stimulation device monitors the heart of the patient and, if two consecutive intrinsic heartbeats are detected, overdrive pacing is automatically triggered. The overdrive pacing rate is based on the heart rate detected at the time overdrive pacing is triggered and is typically 5 to 10 ppm higher than the intrinsic rate. The intrinsic heart rate may be determined, for example, by calculating the time interval between the two consecutive intrinsic beats. The stimulation device then overdrive paces the heart at the selected overdrive pacing rate for a dwell time consisting of a programmed number of overdrive events or cycles. Thereafter, the stimulation device slowly decreases the overdrive pacing rate by a rate decrement specified by a programmed recovery rate until additional intrinsic beats are detected, then the device repeats the process to determine a new overdrive pacing rate and pace accordingly. If the heart rate is increasing quickly, such as may occur with an episode of tachycardia, the stimulation device may still detect intrinsic beats even while overdrive pacing is being applied. If so, the stimulation device immediately determines a new higher overdrive pacing rate based on the selected response function and the new heart rate. Again, if intrinsic beats are still detected, the overdrive pacing rate is increased per the response function. In this manner, the overdrive pacing rate may quickly be increased to 150 ppm or more in response to a tachycardia such as SVT.

Ultimately, the overdrive rate will be increased to the point where it exceeds the intrinsic rate of the tachycardia and hence no intrinsic beats will be detected. The pacing rate is eventually decreased using rate recovery until two or more consecutive intrinsic beats are again detected and the pacing rate is increased again. Assuming that overdrive pacing has succeeded in terminating the tachycardia, rate recovery will ensure that the pacing rate decreases slowly back down to a normal rate of perhaps 60 to 80 bpm. If a base rate is programmed, such as 60 bpm, the heart will be paced at the base rate even if the recovery rate would otherwise cause the rate to decrease even further. Likewise, if an alternative base rate, such as the rest rate or circadian base rate, is programmed, the pacing rate will not fall below those rates either.

It is believed that overdrive pacing is effective for at least some patients for preventing or terminating the onset of an actual tachycardia for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods, which, in turn, can trigger a tachycardia. By overdrive pacing the heart at a uniform rate, the likelihood of the occurrence of ectopic pulses is reduced and the refractory periods within the heart tissue are rendered uniform and periodic. Thus, the dispersion of refractory periods is reduced and tachycardias triggered thereby are substantially avoided. If a tachycardia nevertheless occurs, overdrive pacing at a rate faster than a tachycardia helps to eliminate ectopic pulses and reduce refractory period dispersion, and thereby helps to terminate the tachycardia.

However, in order for this scheme to work, it must be assured that each overdrive pulse actually triggers an atrial contraction, i.e. that the overdrive pulses are captured by the atria. If overdrive pulses are not captured, i.e. a loss-of-capture (LOC) occurs, intrinsic pulses are typically generated within the heart. The intrinsic pulses may be ectopic pulses of the type triggering tachyarrhythmia. Moreover, even if a tachyarrhythmia does not occur, the presence of the intrinsic pulses may trigger unwanted increases in the overdrive rate resulting in a generally higher overdrive pacing rate than needed. A high overdrive pacing rate has certain disadvantages. For example, the high rate may be unpleasant to the patient, particularly if the artificially-induced heart rate is relatively high in comparison with the heart rate that would otherwise normally occur. A high overdrive rate may also cause possible damage to the heart or may possibly trigger more serious arrhythmias, such as a ventricular fibrillation. A high overdrive rate may be especially problematic in patients suffering from heart failure, particularly if the heart failure is due to an impaired diastolic function and may actually exacerbate heart failure in these patients. Also, a high overdrive rate may be a problem in patients with coronary artery disease because increasing the heart rate decreases diastolic time and decreases perfusion, thus intensifying ischemia.

In an attempt to avoid LOCs during overdrive pacing, conventional devices typically set the magnitude of the overdrive pulses to be quite high so as to assure that the overdrive pulses are captured. Typically the magnitude of each overdrive pulse is set to at least twice the expected capture threshold, i.e. twice the pulse magnitude actually expected to achieve capture. The need to apply overdrive pacing pulses with high pulse magnitude operates to deplete the power supply of the implantable cardiac stimulation device. Since overdrive pacing is preferably performed more or less continuously within many patients, the increased pulse magnitude can have a significant effect on battery longevity perhaps requiring frequent surgical replacement of the device.

Accordingly, it would be desirable to provide an overdrive pacing technique that permits a reduction in the average magnitude of overdrive pacing pulses while still achieving adequate capture to thereby reduce overall power consumption and enhance device longevity while also ensuring that adequate overdrive pacing therapy is delivered to reduce the risk of tachyarrhythmia. It is to this end that the invention is primarily directed.

SUMMARY OF THE INVENTION

In accordance with one aspect of the invention, an overdrive pacing technique is provided with automatic capture verification so as to permit a general reduction in the magnitude of overdrive pacing pulses. The technique is implemented within an implantable cardiac stimulation device having a sensing circuit for sensing electrical signals from the heart of a patient, a pulse generator for generating pacing pulses for delivery to the heart of the patient, and a control unit. The control unit controls the pulse generator to overdrive pace the heart at an overdrive pacing rate with each pulse set to a standard pacing pulse magnitude. The control unit performs capture verification on each overdrive pacing pulse using signals detected by the sensing circuit. If a pulse fails to evoke capture, the pulse generator is controlled to generate a backup pulse having a pulse magnitude greater than a standard overdrive pulse magnitude for delivery to the heart tissue. By providing capture verification of overdrive pacing pulses, the pulse magnitude of each overdrive pulse can be reduced as compared with systems wherein capture verification of overdrive pulses is not performed and wherein, instead, overdrive pulses are merely set to a high pulse magnitude in an attempt to ensure capture. Hence, less power is consumed. Also, by administering a backup pulse whenever a LOC is detected, fewer intrinsic beats arise during overdrive pacing and hence there is less risk of tachyarrhythmia and less risk of unneeded overdrive pacing rate increases.

In accordance with another aspect of the invention, the standard overdrive pulse magnitude is determined by performing an automatic capture threshold detection search. The threshold detection search may be performed, for example, whenever two consecutive overdrive pulses fail to evoke capture or may be performed periodically. In one example, atrial capture thresholds are assessed only during the 'dwell time' of overdrive, i.e. only while the heart rate is being overdriven for a programmed number of cycles. During the capture threshold assessment, the pacing rate is slightly increased above the overdrive rate (e.g. +5 bpm) and the magnitude of the overdrive pulses (either amplitude or pulse width) is decremented every second pulse. When two consecutive LOCs are detected, the overdrive pulse magnitude is incrementally increased until two consecutive captures are detected. A safety margin (typically 0.5 V) is added to the resulting pulse magnitude to yield a new standard overdrive pulse magnitude. A back-up pulse is issued after every beat that is not captured during the capture threshold assessment. By providing for automatic capture threshold detection searches, the standard pulse magnitude of the overdrive pulses can be kept as low as possible while still ensuring that substantially all overdrive pulses are properly captured such that backup pulses are not often needed. This further helps reduce power consumption.

In accordance with other aspects of the invention, a variety of rate recovery techniques are provided for reducing the overdrive rate following a sequence of overdrive pacing pulses. In a first rate recovery technique, capture verification is suspended during rate recovery since it may be difficult to adequately distinguish between overdrive pulses that fail to evoke capture because the pulse magnitude was too low (i.e. a true LOC) and overdrive pulses that fail to evoke capture because an intrinsic electrical heart signal "fuses" with a pacing pulse signal thus preventing the triggering of a heart beat (i.e. a "fusion-based" LOC). Instead of providing capture verification, an elevated pulse magnitude is employed during rate recovery. When a predetermined number of intrinsic beats are detected, the overdrive rate is increased. The overdrive pulse magnitude is maintained at the elevated pulse magnitude for the next two beats and a full capture assessment is performed. If capture is detected, then the pulse magnitude is incrementally reduced over the next two beats. If capture is not detected, the overdrive rate is not increased; rather the pulse amplitude is immediately increased to a high-output mode (HOM) voltage (e.g. 4.5V). A capture threshold search is then initiated to reset to pulse magnitude. By suspending capture verification during rate recovery and instead slightly increasing the pulse magnitude, problems with likelihood of fusion are avoided during rate recovery, yet capture is substantially assured.

In a second rate recovery technique, capture detection is maintained during rate recovery but the pulse magnitude is increased to the HOM voltage. Once the output is increased to HOM, subsequent LOCs are considered to be intrinsic P-waves. When a predetermined number of P-waves are detected, the rate is increased. During a next overdrive dwell time, pacing is resumed at the previous standard pacing pulse magnitude. By increasing the pulse magnitude to HOM during rate recovery, capture is substantially guaranteed. Hence, any detected LOC is probably actually a P-wave and is counted as such. In this manner, problems distinguishing between a true LOC and fusion-based LOC are avoided.

In a third rate recovery technique, capture detection is maintained during rate recovery and the standard pulse magnitude is not changed unless LOCs are detected. A first LOC is not counted for the purposes of rate recovery as either an A-pulse or a P-wave. On the next beat, the pulse magnitude is increased to the HOM voltage and the overdrive rate is incrementally decreased. Once the pulse magnitude is increased to the HOM voltage, subsequent LOCs are counted as P-waves. Whether the response to the next pacing pulse is capture (A-pulse), inhibition by a P-wave, or an LOC, the result is the same: the pulse magnitude is maintained at the HOM voltage and the overdrive rate continues to be decreased until enough P-waves (either true P-waves or LOCs) are detected and the overdrive rate is then increased. During the next overdrive dwell time, a capture threshold test is performed, starting from the previous pacing pulse magnitude. In this manner, the pulse magnitude need not be increased unless and until an LOC is detected.

Method and apparatus embodiments are provided.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
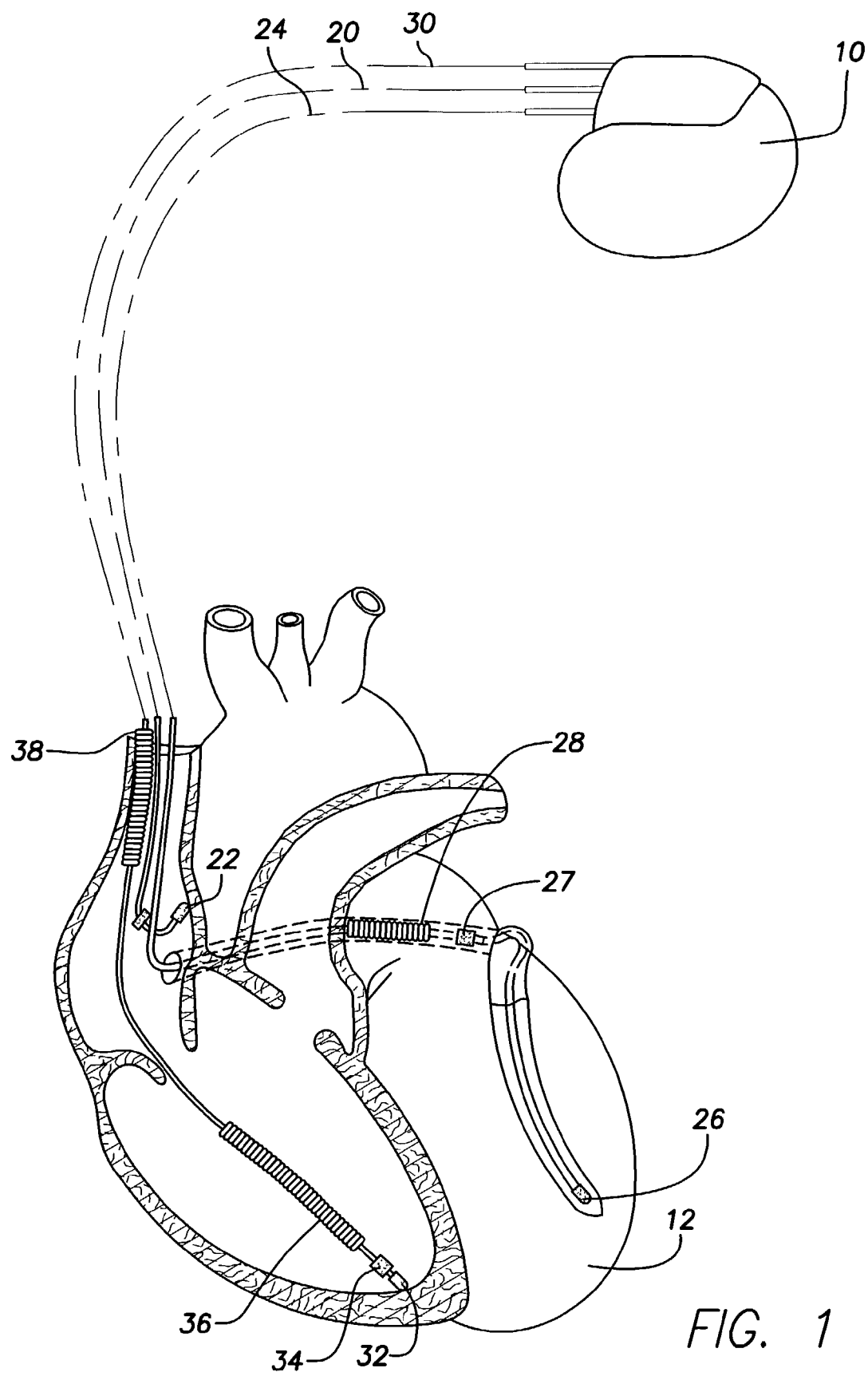
FIG. 1 is a simplified diagram illustrating an implantable stimulation device in electrical communication with at least three leads implanted into the heart of a patient for delivering multi-chamber stimulation and shock therapy and configured in accordance with the invention to perform overdrive pacing.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patent is hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
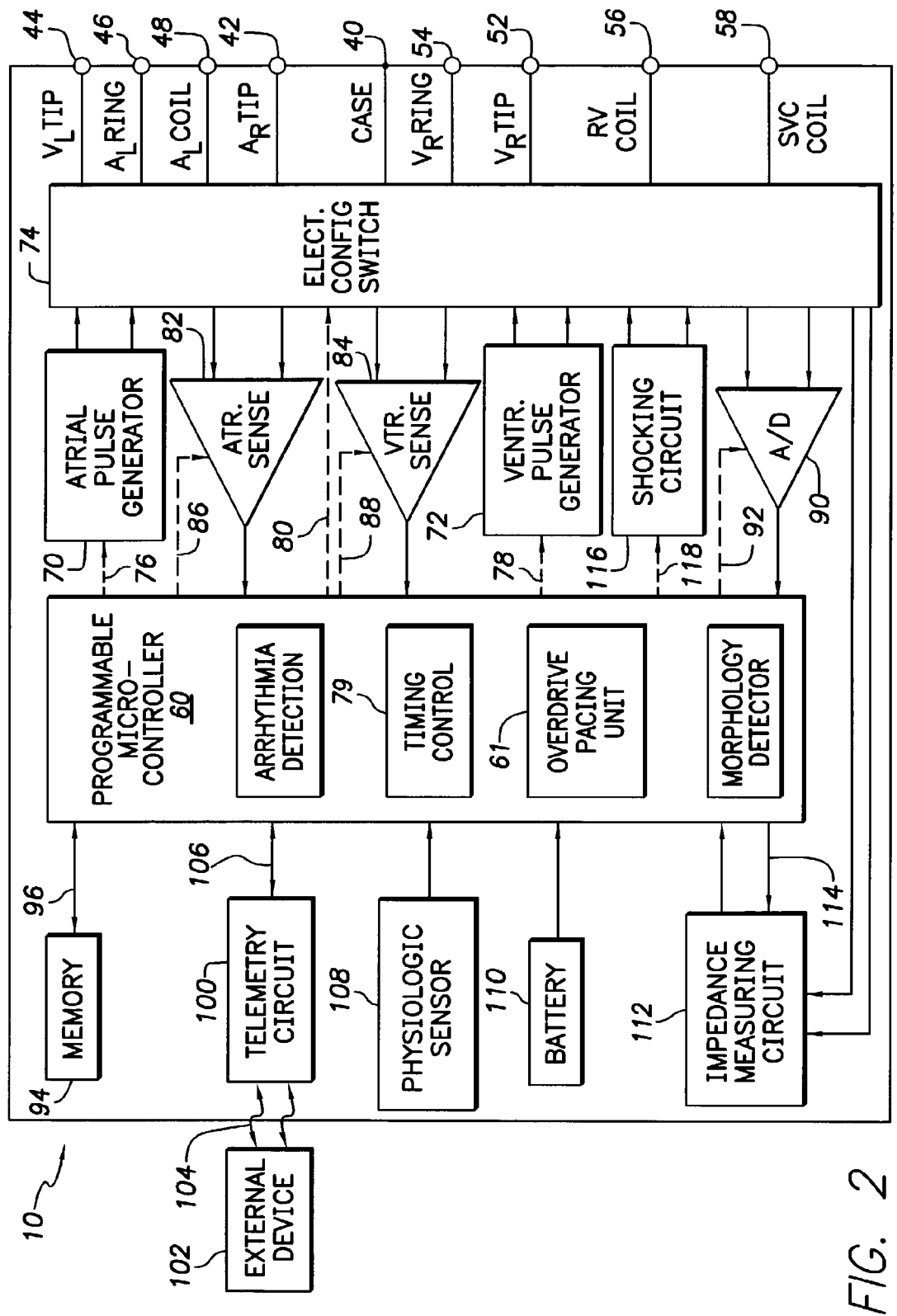
FIG. 2 is a functional block diagram of the implantable cardiac stimulation device of FIG. 1 illustrating basic elements of a stimulation device.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art. Representative types of control circuitry that may be used with the invention include the microprocessor-based control system of U.S. Pat. No. 4,940,052 (Mann et al.), the state-machine of U.S. Pat. No. 4,712,555 (Sholder) and U.S. Pat. No. 4,944,298 (Sholder).

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

The microcontroller includes an overdrive pacing unit 61 for controlling overdrive pacing based on a set of additional control parameters including an overdrive pacing response function, a number of overdrive events; and a recovery rate.

The overdrive pacing response function specifies the overdrive pacing rate to be applied when overdrive pacing is triggered. Overdrive pacing is triggered upon the detection of two consecutive intrinsic heart beats. The number of overdrive events specifies the number of consecutive beats to be paced following triggering of a sequence of overdrive pacing beats. The recovery rate specifies a rate decrement by which the overdrive pacing rate is to be decreased after the number of overdrive events have been paced. As will be described in detail below, the overdrive pacing unit performs capture verification of overdrive pacing pulses and administers backup pulses in the event of LOC. The overdrive unit also performs automatic capture threshold detection searches during the overdrive pacing dwell time to reset the magnitude of the overdrive pulses if needed. The capture threshold detection searches are performed either periodically or in response to two or more LOCs within a single dwell time. The overdrive pacing unit also controls rate recovery in accordance with one of a variety of techniques.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Capture Verification Method

Figure 3:
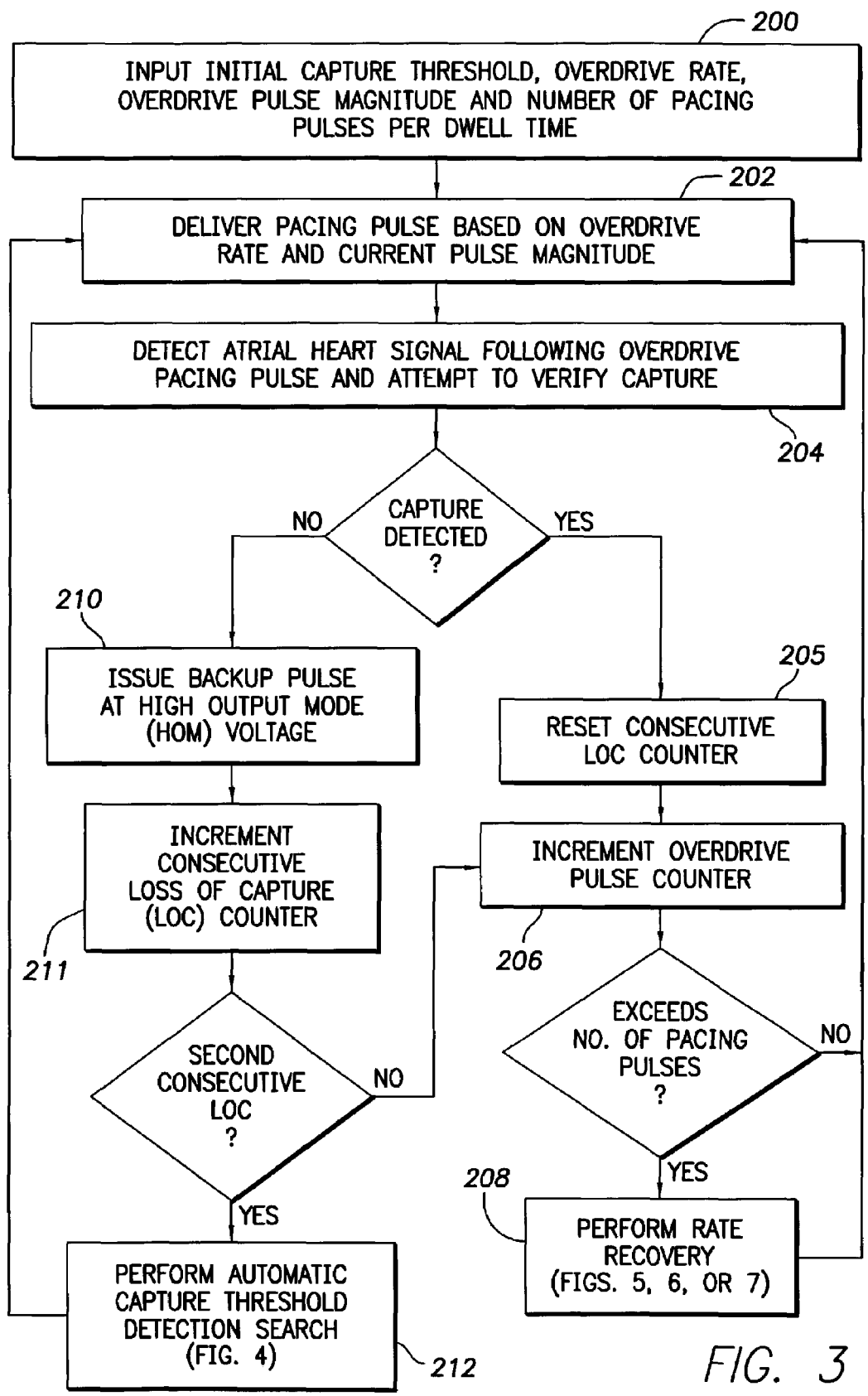
FIG. 3 is a flow chart providing an overview of the operation of an exemplary embodiment of the invention particularly illustrating the manner by which the implantable stimulation device of FIGS. 1 and 2 performs capture verification of overdrive pacing pulses.

Referring first to FIG. 3, a flow chart is shown describing an overview of the operation and novel features of stimulation device 10 as configured in accordance with the first embodiment of the invention. In this flow chart, and the other flow charts described herein, the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

More specifically, FIG. 3 illustrates an automatic capture verification method for use during overdrive pacing to verify that overdrive pacing pulses are properly captured by the heart, i.e. to ensure that the overdrive pacing pulses actually trigger a corresponding heart beat. Upon initial entry into an overdrive pacing mode, at step 200, the overdrive pacing unit (unit 61 of FIG. 2) inputs an initial capture threshold, an initial overdrive rate, an initial overdrive pulse magnitude and a number of pacing pulses per dwell time for use in overdrive pacing the heart. Preferably, the pulse magnitude is representative of the total pulse energy, rather than just pulse amplitude or pulse width. The capture threshold represents the minimum current overdrive pulse magnitude sufficient to achieve capture. Suitable initial values may be as follows: initial capture threshold—2.0 volts; initial overdrive pulse magnitude—the initial capture threshold plus a safety margin of 0.5 volts; initial overdrive rate—five beats above the current intrinsic heart rate; and initial dwell time—20 paced beats. The initial values may be pre-programmed within the device or may be derived from a pervious overdrive pacing session. In the case of the initial overdrive rate, it is preferably set based on the most recently measured intrinsic heart rate. By setting the pulse magnitude based on the capture threshold plus a safety margin, it is reasonably assured that overdrive pulses will be captured by the heart tissue and thereby will trigger a heartbeat. As will be explained, the capture threshold, pulse magnitude and overdrive rate are continuously adjusted for optimal overdrive pacing based on the remaining steps of the figures. Also, at step 200, various counters, including an Overdrive Pacing Pulse Counter and a Consecutive LOC Counter, are initialized to zero.

At step 202, the overdrive pacing unit commences overdrive pacing by delivering an overdrive pacing pulse at the initial pulse magnitude and, at step 204, detects the magnitude of the responsive atrial heart signal following the overdrive pulse to verify capture. If capture was achieved, the Consecutive LOC Counter is reset to zero at step 205 and the Overdrive Pacing Pulse Counter is incremented at step 206. Processing returns to step 202 for delivery of another overdrive pacing pulse. Capture may be verified, for example, by comparing the magnitude of the atrial signal (i.e. the atrial electrical response plus a known polarization value) against a predetermined atrial signal threshold value and, if the atrial signal exceeds the threshold value, capture is verified; otherwise, an LOC has occurred. In the alternative, capture verification is achieved by maintaining a running average (i.e. mean) and a variation (i.e. mean average variation or standard deviation) of the detected atrial signal magnitude and determining whether a change in the atrial signal magnitude exceeds a permissible degree of variation. In any case, so long as each pulse is captured, the Overdrive Pacing Pulse Counter is repeatedly incremented until the dwell time for the current sequence of overdrive pacing is exceeded, whereupon rate recovery is performed at step 208 using one of the techniques of FIGS. 5–7, which will be described below, to establish a new lower overdrive rate. Then a new sequence of overdrive pacing pulses commences again beginning at step 202.

If, however, any of the overdrive pacing pulses are not captured by the atria (i.e. a LOC has been detected) then, following step 204, a backup pacing pulse is delivered at step 210. The backup pulse is set to the HOM voltage of, for example, 4.5V and is delivered 40 ms after the pulse that failed to evoke capture. The Consecutive LOC Counter is incremented at step 211. If the LOC is a first LOC, processing simply continues at step 202 for further overdrive pacing. However, upon detection of a second consecutive LOC during the dwell time, the overdrive unit performs an automatic capture threshold detection search at step 212 using the technique of FIG. 4 to set a new capture threshold and a new pulse magnitude. Thereafter, the next sequence of overdrive pacing pulses is generated using the new pulse magnitude. Thus two consecutive LOCs trigger a capture threshold detection search. A capture detected subsequent to a first LOC will reset the Consecutive LOC Counter at step 205 so that the next LOC will not immediately trigger the capture threshold detection search.

By automatically detecting the capture threshold and by adjusting the pulse magnitude to remain above the threshold, subsequent overdrive pacing pulses should properly evoke capture thereby eliminating any further LOC events, at least in the near future. Eventually, changes in the electrical characteristics of the heart or use of medications may result in further LOCs triggering a new capture threshold detection search. Also, capture threshold detection searches are also performed periodically regardless of whether any LOC events have been detected, to lower the capture threshold when warranted. In this manner, the pulse magnitude is kept as low as possible while still evoking capture, to thereby consume as little battery power as possible while still ensuring adequate capture of overdrive pacing pulses.

Capture Threshold Detection Method

Figure 4:
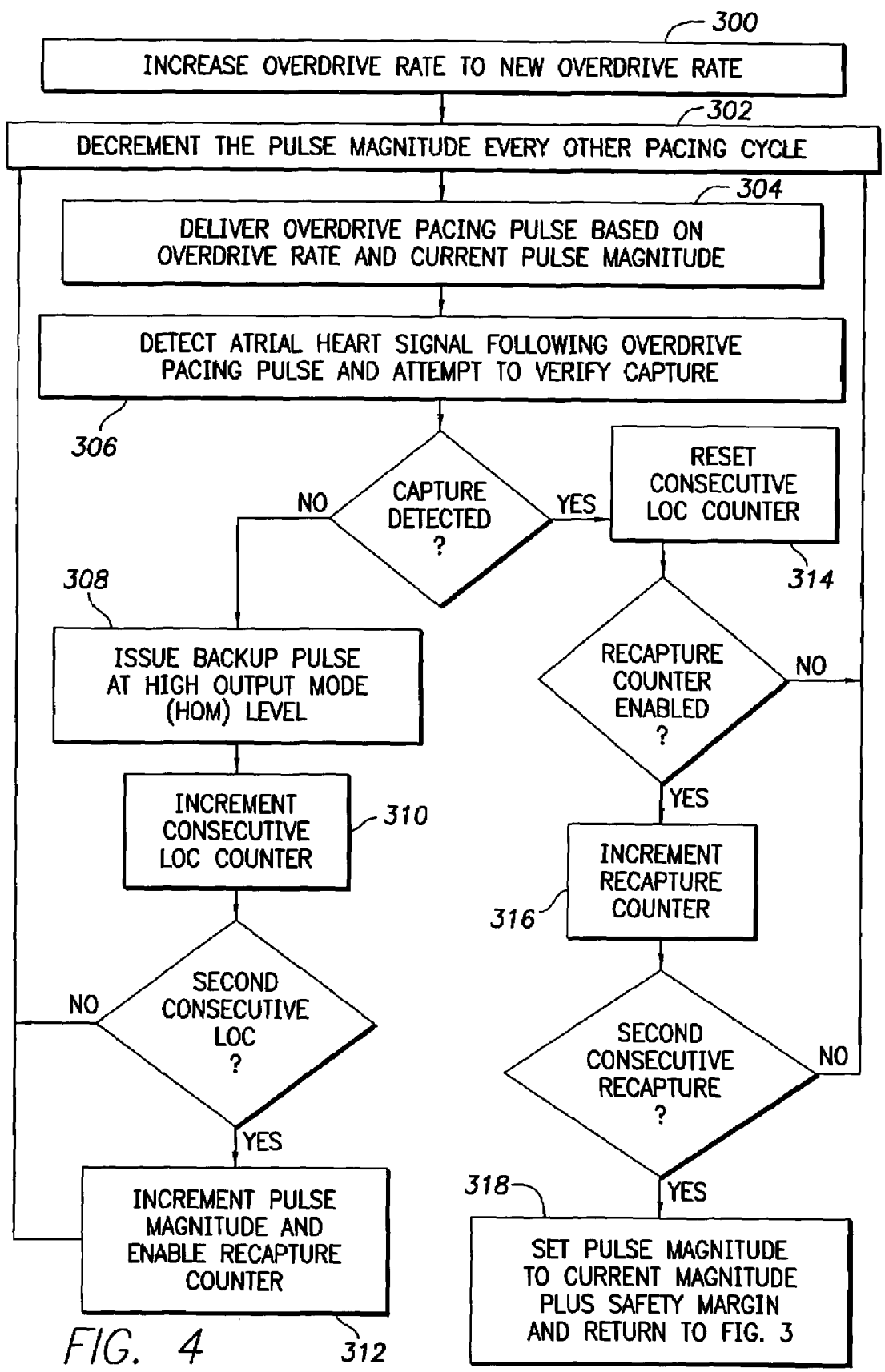
FIG. 4 is a flow chart particularly illustrating the manner by which the implantable stimulation device performs an automatic capture threshold detection search.

FIG. 4 illustrates an automatic capture threshold detection method for use at step 212 of the capture verification method of FIG. 3 to determine a new capture threshold. Briefly, the atrial capture threshold is assessed during the overdrive dwell time. During the capture threshold search, the pacing rate is slightly increased above the overdrive rate and the pulse magnitude is decremented every other pulse. When two consecutive LOCs are detected, the overdrive pulse magnitude is incrementally increased until two consecutive captures are detected. A back-up pulse is issued after every beat that is not captured. The capture threshold detection search is performed periodically and is also performed following detection of two consecutive LOCs within a single overdrive pacing dwell time. If triggered by two LOCs, then a LOC recovery processes is preferably performed following the second LOC and before the capture threshold detection search of FIG. 4 begins. The LOC recovery process consists of incrementally increasing the pulse magnitude until two consecutive captures are detected.

Now considering the method of FIG. 4 in greater detail, upon initial entry into the capture detection mode, the overdrive pacing unit, at step 300, increases the overdrive rate to a new higher overdrive rate to help ensure that no intrinsic atrial events occur during the threshold detection search. Typically, the overdrive rate is increased by 5 ppm. At step 302, the overdrive unit decrements the current pulse magnitude by a preprogrammed pulse magnitude decrement (e.g. 0.25V) then, at step 304, delivers a pacing pulse at the new lower pulse magnitude. The magnitude of the responsive heart signal is detected at step 306 and to verify capture. If the pulse was not captured, a backup pulse is delivered at the HOM voltage at step 308 and a Consecutive LOC Counter is incremented at step 310 for use in counting consecutive LOC events. Processing then continues at step 302 wherein the pulse magnitude is further decremented every other cycle. Another pulse is delivered and capture verification is again performed. If a second consecutive LOC is detected, the overdrive unit increases the pulse magnitude by a preprogrammed pulse magnitude increment (e.g. 0.125V) at step 312 and enables the counting of post-LOC beats using a Recapture Counter. Since the pulse magnitude has been increased, the next overdrive pulse will not likely fail to evoke capture and another backup pulse will probably not needed. If however, a third consecutive LOC is detected, the overdrive unit delivers another backup pulse at step 308 and increases the pulse magnitude again at step 312. In any case, eventually capture is evoked and the overdrive unit then resets the Consecutive LOC Counter at step 314 then increments the Recapture Counter at step 316 to begin counting post-LOC events.

Upon detection of a first recapture event following the previous two consecutive LOCs, processing simply returns to step 302 for delivery of another overdrive pulse. Upon detection of a second recapture event, however, step 318 is instead performed wherein the standard pulse magnitude is reset to be equal to the current pulse magnitude plus a safety margin of 0.5 volts. Thus, if the pulse magnitude, as a result of the various increments and decrements of the steps of FIG. 4 is adjusted to 2.0 volts, the overdrive unit re-sets the pulse magnitude to 2.5 volts at step 318. The threshold detection search is thus complete and processing returns to step 212 of FIG. 3 for further overdrive pacing using the newly reset pulse magnitude.

Thus the pulse magnitude is decremented every other pulse until two consecutive LOCs are detected, then the pulse magnitude is increased slightly until two consecutive captures are again evoked. The resulting pulse magnitude represents the new capture threshold. Note that the steps of FIG. 4 are performed only during the dwell time of overdrive pacing. In the example of FIG. 4, overdrive pacing continues as long as needed to reset the pulse magnitude, i.e. the dwell time is not tracked. Alternatively, the overdrive pacing unit may continue to track the dwell time and perform a rate reduction upon completion of the dwell time even if a new pulse magnitude has not been identified. If so, then preferably, the dwell time is doubled over its normal duration, e.g. forty paced beats instead of only twenty paced beats, before rate recovery is triggered.

Rate Recovery Methods

Figure 5:
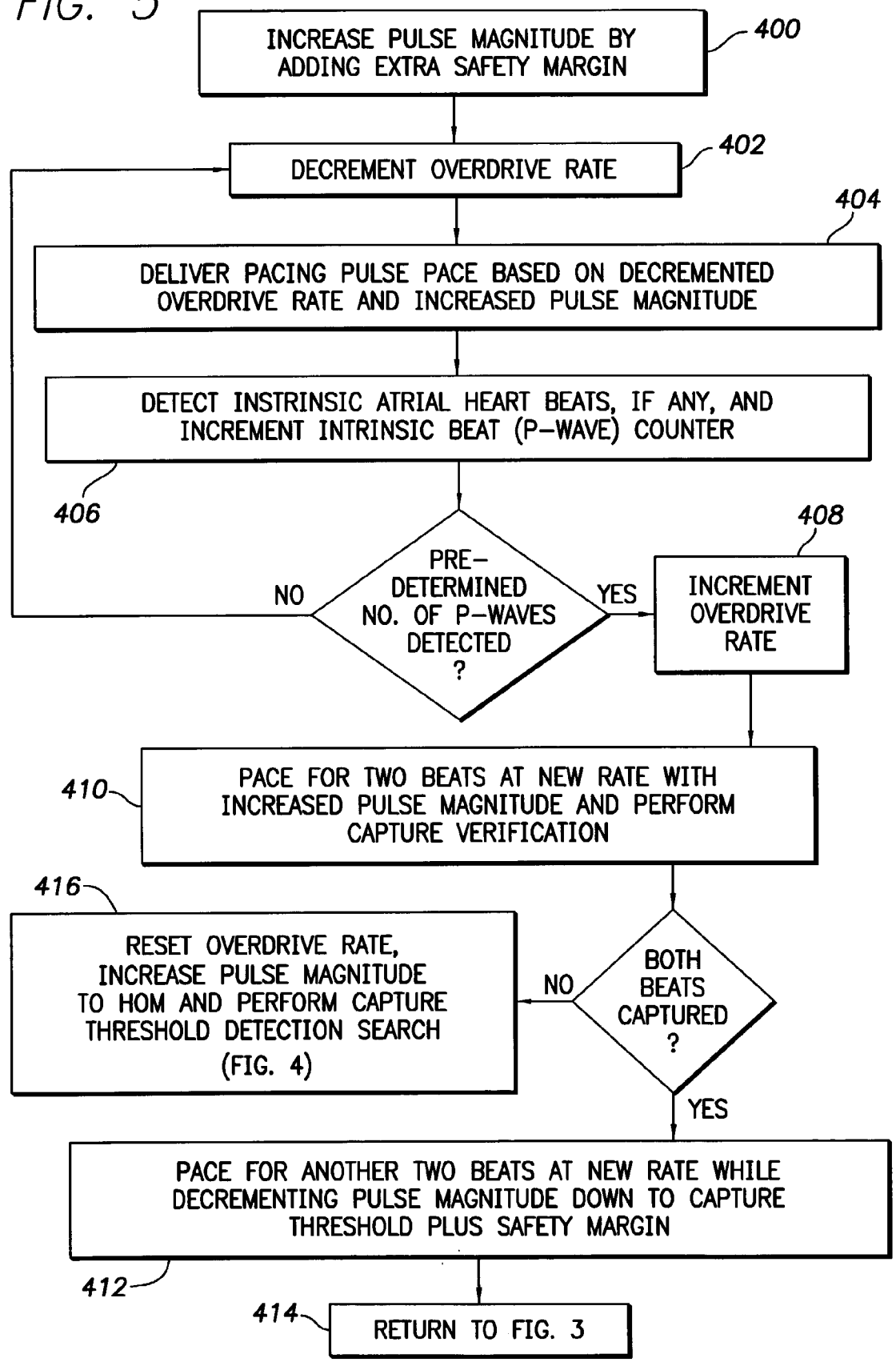
FIG. 5 is a flow chart particularly illustrating the manner by which the implantable stimulation device performs rate recovery while suspending capture verification.
Figure 6:
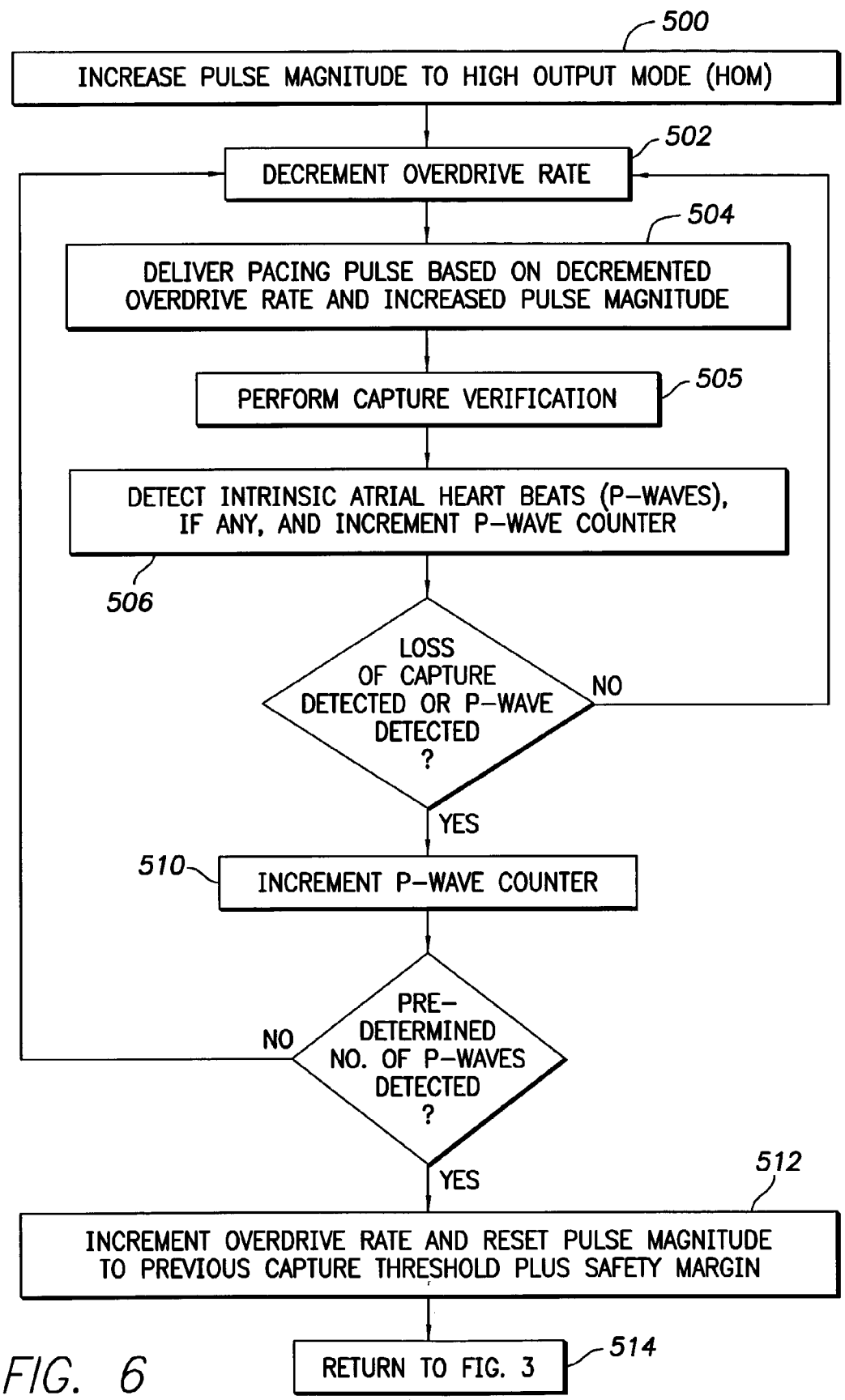
FIG. 6 is a flow chart illustrating an alternative technique for performing rate recovery wherein capture verification is maintained during rate recovery.
Figure 7:
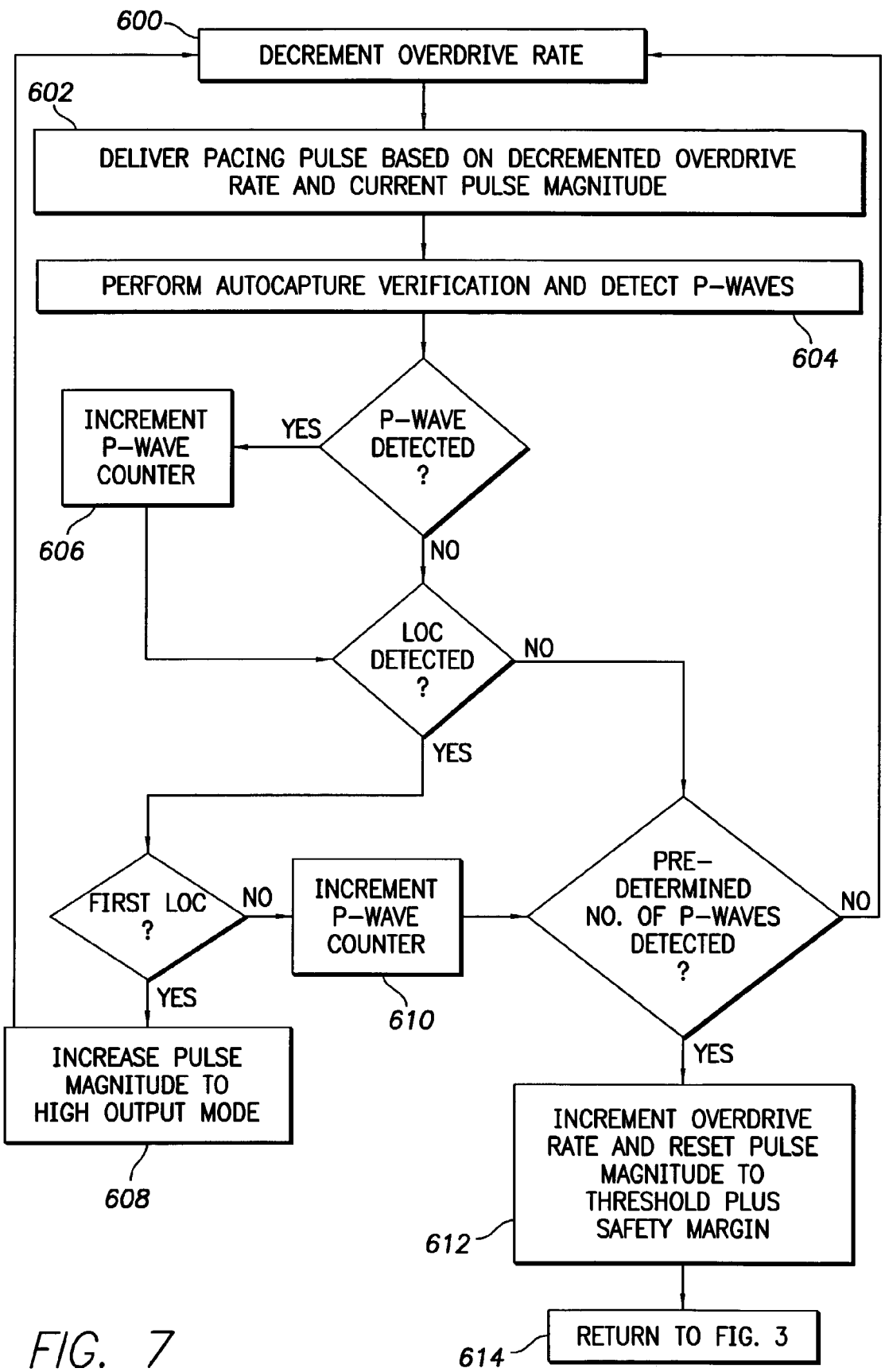
FIG. 7 is a flow chart illustrating yet another alternative technique for performing rate recovery.

FIGS. 5–7 illustrate three alternative rate recovery methods for use during overdrive pacing to reduce the overdrive rate for use at step 210 of the capture verification method of FIG. 3.

Referring to FIG. 5, a rate recovery method is illustrated wherein capture verification is suspended during rate recovery to avoid possible misidentification of intrinsic beats as a result of fusion and an elevated pulse magnitude is employed. Briefly, when a predetermined number of intrinsic beats are detected, the overdrive rate is increased, the overdrive pulse magnitude is maintained at the elevated pulse magnitude for the next two beats, and a full capture assessment is performed. If capture is detected, the pulse magnitude is incrementally reduced over the next two beats. If capture is not detected, the overdrive rate is not increased; rather the pulse amplitude is immediately increased to the HOM voltage. A capture threshold search is then initiated to reset the pulse magnitude.

Considering the method of FIG. 5 in greater detail, upon initial entry into the rate recovery mode, the overdrive pacing unit, at step 400, increases the pulse magnitude by doubling the safety margin to help ensure that loss of capture does not occur. At step 402, the current overdrive pacing rate is decremented by a preprogrammed rate recovery value (e.g. 5 ppm) then, at step 404, a pacing pulse is delivered based on the new rate. The overdrive pacing unit monitors the atrial heart signal at step 406 to detect and count any intrinsic beats, i.e. P-waves, found therein. Until some predetermined threshold number of P-waves is detected, typically two P-waves, steps 402–406 are repeated to periodically lower the overdrive rate. Once the predetermined number of P-waves has been detected, step 408 is performed to increase the overdrive rate by the recovery rate value in an attempt to ensure that further P-waves do not occur. In this manner, the overdrive rate is set to the lowest rate expected to ensure that few, if any, P-waves occur. The overdrive pacing unit then delivers two pacing pulses at the new overdrive rate at step 410 with a doubled safety margin and capture verification is performed. If both beats are properly captured, then the overdrive pacing unit completes the rate recovery process, at step 412, by pacing for two more beats while decrementing the pulse magnitude back down to the current capture threshold plus a single safety margin. A new overdrive rate is thereby established and processing returns to step 208 of FIG. 3 via step 414. If either of the two beats of step 410 results in a LOC, then the overdrive pacing unit instead performs step 416 wherein the rate increase of step 408 is abandoned, the pulse magnitude is increased to the HOM voltage and a new threshold detection search is immediately performed using the method of FIG. 4.

In the technique of FIG. 5, by suspending capture verification during rate recovery and instead slightly increasing the pulse magnitude, problems with likelihood of fusion are avoided during rate recovery, yet capture is substantially assured.

Referring to FIG. 6, a rate recovery method is illustrated wherein capture verification is maintained during rate recovery but the pulse magnitude is increased to the HOM voltage to help eliminate LOC events which might result in misidentification of intrinsic beats as a result of fusion. Once the output is increased to HOM, subsequent LOCs are counted as P-waves and, when a predetermined number of P-waves are detected, the rate is increased. During the next overdrive pacing dwell time, pacing is resumed at the previous pacing pulse magnitude.

Now considering the technique of FIG. 6 in more detail, upon initial entry into the rate recovery mode, the overdrive pacing unit increases the pulse magnitude to the HOM voltage, at step 500, to help ensure that loss of capture does not occur. At step 502, the current overdrive pacing rate is decremented by the preprogrammed rate recovery value and, at step 504, a pacing pulse is delivered at the HOM voltage at the new overdrive rate. The overdrive pacing unit performs capture verification at step 505 to detect a possible LOC and monitors the atrial heart signal at step 506 to detect any intrinsic beats, i.e. P-waves, occurring subsequent to the pacing pulse. If no LOCs and no P-waves are detected, processing simply returns to step 502 for a further reduction in the overdrive rate. If either a P-wave or a LOC is detected, a P-wave Counter is incremented at step 510 and processing return to step 502 for another reduction in pacing rate. By incrementing the P-wave Counter whenever either a P-wave or a LOC is detected, LOCs are thereby counted as P-waves. After the pre-determined threshold number of P-waves has been counted, at step 512, the pulse magnitude is reduced from the HOM voltage to its previous value and the overdrive rate is increased by the rate recovery value. The pre-determined number of P-waves is typically set to two. Rate recovery is thereby complete and processing returns via step 514 of FIG. 6 to step 208 of FIG. 3 for further overdrive pacing at the new overdrive rate. In this manner, the overdrive rate is thereby set to the lowest rate expected to ensure that relatively few P-waves occur.

In the technique of FIG. 6, by increasing the pulse magnitude to the HOM voltage, LOCs can be reliably counted as P-wave and problems involving possible misidentification of LOCs and P-waves as a result of fusion are thereby avoided.

Referring to FIG. 7, another rate recovery method is provided wherein capture verification is maintained during rate recovery but wherein pulse magnitudes are not increased to the HOM voltage unless a LOC is detected during rate recovery. The LOC may be either the result of fusion or may be an actual LOC. In either case, the LOC is not counted for the purposes of overdrive pacing as either an A-pulse or a P-wave. On the next beat, the pulse amplitude is increased to the HOM voltage and the cycle length is extended. After the output has been increased to the HOM voltage, subsequent LOCs are considered to be P-waves. Whether the response to the next pacing pulse is capture, an inhibition by a P-wave, or is classified as LOC, the method same steps are preformed: the pulse magnitude is maintained at the HOM voltage and the cycle length continues to be extended until enough P-waves (either true P-waves or LOCs) are detected and the rate is then increased. During the next overdrive dwell time, a capture threshold test is performed, starting from the previous pacing pulse energy.

Now considering the technique of FIG. 7 in more detail, upon initial entry into the rate recovery mode, the overdrive pacing unit, at step 600, decrements the current overdrive pacing rate and, at step 602, delivers a pacing pulse based on the new rate and the current pulse magnitude. The overdrive pacing unit performs capture verification at step 604 to detect a possible LOC and also monitors the atrial heart signal to detect any P-waves occurring subsequent to the pacing pulse. If no P-waves or LOCs are detected, processing simply returns to step 600 for a further reduction in the overdrive rate. Whenever a P-wave is detected, a P-wave Counter is incremented at step 606. When a first LOC is detected, the pulse magnitude is increased to the HOM voltage at step 608. When a second LOC is detected, the P-wave Counter is incremented at step 610. In this manner, LOCs are thereafter counted as P-waves. Until a predetermined number of P-waves have been counted (typically two), processing always returns to step 600 for further reductions in pacing rate. Once the predetermined number of P-waves has been counted, the pulse magnitude is reduced from the HOM voltage to its previous value at step 612 and the overdrive rate is increased. Processing returns via step 614 of FIG. 7 to step 208 of FIG. 3 for further overdrive pacing at the new overdrive rate.

In the technique of FIG. 7, by increasing the pulse magnitude to the HOM voltage only after a first LOC is detected, overall power reduction is achieved, yet problems involving possible misidentification of LOCs and P-waves as a result of fusion are still avoided.

In the forgoing, various exemplary techniques have been described wherein a fixed number of paced beats, consecutive LOCs or consecutive re-captures (typically two) is used to trigger particular device operations, such as triggering a capture threshold detection search (step 212 of FIG. 3) or triggering a reset of the pulse magnitude (step 318 of FIG. 4). It should be understood that the system could be configured to employ other fixed numbers of events. For example, the number of consecutive LOCs needed to trigger a capture threshold detection search step 212 of FIG. 3 might instead be set to three or the number of consecutive re-captures needed to trigger a reset of the pulse magnitude at step 318 of FIG. 4 might instead be set to four. Moreover, the system can be configured to employ programmable values, thereby permitting the physician to specify the values.

What have been described are various techniques for performing capture verification of overdrive pacing pulses. Although described primarily with reference to atrial overdrive pacing, the techniques of the invention may be exploited for either atrial or ventricular overdrive pacing. Also, although described primarily with reference to an example wherein the implanted device is a defibrillation/pacer, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device having a sensing circuit for sensing electrical signals from heart tissue of a patient, a pulse generator for generating pacing pulses for delivery to the heart of the patient and a control unit, a method performed by the control unit comprising the steps of:

controlling the pulse generator to overdrive pace the heart at a selected overdrive pacing rate which is higher than intrinsic heart rate of the patient, with each pulse set to a standard overdrive pacing pulse magnitude; and performing capture verification for each overdrive pacing pulse using the sensing circuit and, if a pulse fails to evoke capture, controlling the pulse generator to deliver a backup pulse to the heart tissue at a pulse magnitude greater than the standard overdrive pulse magnitude.

2. The method of claim 1 wherein the step of performing capture verification includes the steps of:

comparing an electrical heart signal detected by the sensing circuit subsequent to each pacing pulse with a predetermined threshold; and determining that capture has not been evoked for particular pulse if the detected electrical heart signal falls below the threshold.

3. The method of claim 1 further including the step of performing an automatic capture threshold detection search to determine a new pulse magnitude for use as the standard overdrive pulse magnitude.

4. The method of claim 3 wherein the automatic capture threshold search is performed whenever a pre-programmed number of consecutive overdrive pulses fail to evoke capture.

5. The method of claim 3 wherein the automatic capture threshold search is performed whenever at least two consecutive overdrive pulses fail to evoke capture.

6. The method of 3 wherein the automatic capture threshold search is performed periodically.

7. The method of claim 3 wherein the step of controlling the pulse generator to overdrive pace the heart at a selected overdrive pacing rate is performed for a predetermined number of cycles.

8. The method of claim 7 wherein the automatic capture threshold detection search is performed during the predetermined number of overdrive cycles.

9. The method of claim 3 wherein the step of performing an automatic capture threshold detection search includes the steps of:

controlling the pulse generator to overdrive pace the heart at rate higher than the selected overdrive pacing rate while incrementally decreasing a current pulse magnitude;

performing capture verification following each overdrive pacing pulse until at least two consecutive overdrive pulses fail to evoke capture, then incrementally increasing the current pulse magnitude until at least two consecutive overdrive pulses again evoke capture; and setting a new standard pulse magnitude based on the resulting current pulse magnitude.

10. The method of claim 9 further including the step, performed subsequent to each capture verification, of delivering a backup pulse to the heart tissue at a pulse magnitude greater than the standard overdrive pulse magnitude, with the backup pulse being delivered regardless of whether the prior overdrive pulse failed to evoke capture.

11. The method of claim 9 wherein the step of controlling the pulse generator to overdrive pace the heart at the selected overdrive pacing rate is performed for a predetermined number of cycles and wherein the predetermined number of cycles in automatically increased upon commencement of automatic capture threshold search.

12. The method of claim 1 further including the steps, performed by the control unit, of:
controlling the pulse generator to incrementally decrease the overdrive pacing rate while generating overdrive pacing pulses at the standard overdrive pacing pulse magnitude plus a predetermined safety margin;
detecting intrinsic heart signals, if any, using the sensing circuit; and
if a predetermined number of intrinsic heart signals are detected, increasing the overdrive rate to a new overdrive rate.

13. The method of claim 12 wherein the predetermined number of intrinsic heart signals is a programmable value.

14. The method of claim 12 wherein the predetermined number of intrinsic heart signals is at least two.

15. The method of claim 12 further including the steps, performed subsequent to the increase of the overdrive rate to the new overdrive rate, of:
performing capture verification on the next two consecutive pacing pulses and if either pulse fails to evoke capture, increasing the pulse magnitude to a predetermined high pulse magnitude and performing an automatic capture threshold detection search to determine a new pulse magnitude for use as the standard overdrive pulse magnitude.

16. The method of claim 15 further including the step, performed if bath pulses evoke capture, of incrementally decreasing the standard overdrive pulse magnitude over the next two overdrive beats to yield a new the standard overdrive pulse magnitude, then continuing overdrive pacing at the new standard overdrive pulse magnitude.

17. The method of claim 1 further including the steps, performed by the control unit, of:
controlling the pulse generator to generate overdrive pacing pulses at an incrementally decreasing overdrive pacing rate, with each pulse set to a predetermined high pulse magnitude;
performing capture verification following each overdrive pacing pulse to identify loss of capture events;
receiving electrical signals from the sensing circuit representative of true intrinsic heart signals; and
upon detection of a predetermined total combined number of intrinsic heart signals and loss of capture events occurring, increasing the standard overdrive rate by a predetermined amount then resuming overdrive pacing at the new standard overdrive pacing pulse magnitude.

18. The method of claim 1 further including the steps, performed by the control unit, of:
controlling the pulse generator to generate overdrive pacing pulses at an incrementally decreasing overdrive pacing rate, with each pulse set to the standard overdrive pacing pulse magnitude;
performing capture verification following each overdrive pacing pulse to identify loss of capture events;
receiving electrical signals from the sensing circuit representative of true intrinsic heart signals;
if a predetermined number of intrinsic heart signals are detected, increasing the current overdrive rate by a predetermined amount then resuming overdrive pacing at the standard overdrive pacing pulse magnitude; and
if a predetermined number of loss of capture events are detected, increasing the pulse magnitude to a predetermined high pulse magnitude.

19. The method of claim 18 further including the steps, performed subsequent to the step of increasing the pulse magnitude to a predetermined high output mode magnitude, of:
controlling the pulse generator to generate overdrive pacing pulses at an incrementally decreasing overdrive pacing rate;
performing capture verification following each overdrive pacing pulse using the sensing circuit to identify loss of capture events;
receiving electrical signals from the sensing circuit representative of true intrinsic heart signals; and
upon detection of a predetermined total combined number of intrinsic heart signals and loss of capture events, increasing the current overdrive rate by the predetermined amount then resuming overdrive pacing at the standard overdrive pacing pulse magnitude.

20. The method of claim 19 further including the steps, performed subsequent to the step of resuming overdrive pacing at the standard overdrive pacing pulse magnitude, of performing an automatic capture threshold detection search to determine a new pulse magnitude for use as the standard overdrive pulse magnitude.

21. In an implantable cardiac stimulation device having a sensing circuit for sensing electrical signals from heart tissue of a patient, a pulse generator for generating pacing pulses for delivery to the heart of the patient and a control unit, a method performed by the control unit comprising the steps of:
performing an automatic capture threshold detection search to determine a pulse magnitude for use as a standard overdrive pulse magnitude by
controlling the pulse generator to overdrive pace the heart at rate higher than a previous overdrive pacing rate while incrementally decreasing a current standard pulse magnitude,
performing capture verification following each overdrive pacing pulse using the sensing circuit until at least two consecutive overdrive pulses fail to evoke capture, then incrementally increasing the current pulse magnitude until at least two consecutive overdrive pulses again evoke capture, and
setting a new standard pulse magnitude based on the resulting current pulse magnitude; and
controlling the pulse generator to overdrive pace the heart at the selected overdrive pacing rate using the new standard pulse magnitude while performing capture verification on each overdrive pacing pulse using the sensing circuit.

22. An implantable cardiac stimulation device having:
a sensing circuit operative to receive electrical signals from heart tissue of a patient;
a pulse generator operative to generate pacing pulses for delivery to the heart of the patient; and
an overdrive pacing control unit operative to control the pulse generator to overdrive pace the heart at a selected overdrive pacing rate which is higher than intrinsic heart rate of the patient, with each pulse set to a standard overdrive pacing pulse magnitude, perform capture verification on each overdrive pacing pulse and, for each pulse that fails to evoke capture, deliver a backup pulse to the heart tissue at a pulse magnitude greater than the standard overdrive pulse magnitude.

23. An implantable cardiac stimulation device having:

means for sensing electrical signals from heart tissue of a patient;

means for generating pacing pulses for delivery to the heart of the patient;

means for controlling the means for generating pacing pulses to overdrive pace the heart at a selected overdrive pacing rate which is higher than intrinsic heart rate of the patient, with each pulse set to a standard overdrive pacing pulse magnitude;

means for controlling the sensing circuit to perform capture verification on each overdrive pacing pulse; and means, operative in response to a pulse that fails to evoke capture, for controlling the means for generating pacing pulses to deliver a backup pulse to the heart tissue at a pulse magnitude greater than the standard overdrive pulse magnitude.

* * * * *